US007910556B2

(12) United States Patent
Ishiwata et al.

(10) Patent No.: US 7,910,556 B2
(45) Date of Patent: Mar. 22, 2011

(54) PAR-2 AGONIST

(75) Inventors: Hiroyuki Ishiwata, Chiba (JP);
Mototsugu Kabeya, Tokyo (JP); Toru Kanke, Tokyo (JP)

(73) Assignee: Kowa Company, Ltd., Nagoya-shi (JP)

( * ) Notice: Subject to any disclaimer, the term of this patent is extended or adjusted under 35 U.S.C. 154(b) by 373 days.

(21) Appl. No.: 11/722,952

(22) PCT Filed: Dec. 27, 2005

(86) PCT No.: PCT/JP2005/023852
§ 371 (c)(1),
(2), (4) Date: Jul. 14, 2008

(87) PCT Pub. No.: WO2006/070780
PCT Pub. Date: Jul. 6, 2006

(65) Prior Publication Data
US 2009/0131330 A1 May 21, 2009

Related U.S. Application Data

(60) Provisional application No. 60/639,403, filed on Dec. 28, 2004.

(51) Int. Cl.
*A61K 38/07* (2006.01)
*C07K 5/10* (2006.01)
(52) U.S. Cl. .................... 514/21.9; 514/1.1; 530/330
(58) Field of Classification Search .................... None
See application file for complete search history.

(56) References Cited

U.S. PATENT DOCUMENTS

| | | | |
|---|---|---|---|
| 5,763,575 A | 6/1998 | Sundelin et al. | |
| 5,874,400 A | 2/1999 | Sundelin et al. | |
| 5,888,529 A | 3/1999 | Bunnett et al. | |
| 5,958,407 A | 9/1999 | Bunnett et al. | |
| 7,056,942 B2 * | 6/2006 | Hildesheim et al. | 514/411 |
| 2003/0166553 A1 | 9/2003 | Araki et al. | |
| 2003/0203849 A1 | 10/2003 | Araki et al. | |
| 2004/0077612 A1 * | 4/2004 | Mercep et al. | 514/175 |
| 2005/0222384 A1 | 10/2005 | Ramage et al. | |
| 2006/0019904 A1 | 1/2006 | Araki et al. | |

FOREIGN PATENT DOCUMENTS

| | | |
|---|---|---|
| JP | 2001-64203 A | 3/2001 |
| JP | 2001-181208 A | 7/2001 |
| JP | 2001-233790 A | 8/2001 |
| WO | WO 96/23225 A1 | 8/1996 |
| WO | 01-47556 A1 | 7/2001 |
| WO | 01-62291 A1 | 8/2001 |
| WO | 03-104268 A1 | 12/2003 |
| WO | WO 2006/104190 A1 | 10/2006 |

OTHER PUBLICATIONS

Vippagunta SR, Brittain HG, Grant DJW, "Crystalline solids," Advanced Drug Delivery Reviews, 2001, 48: 3-26.*

John J. McGuirre et al.; "2-Furoyl-LIGRLO-amide: A Potent and Selective Proteinase-Activated Receptor 2 Agonist", The Journal of Pharmacology and Experimental Therapeutics, vol. 309, No. 3, Jun. 2004, pp. 1124-1131. Cited in the ISR.
Hashem N. Alshurafa et al.; "A protease activated receptor-2 (PAR-2) activating peptide, tc-LIGRLO-NH2, induces protease relase from mast-cells: role in TNF degradation", BMC Pharmacology, vol. 4, No. 12, Jul. 2004, pp. 1-9. Cited in the ISR.
Graeme S. Cottrell et al.; "Trypsin IV, a Novel Agonist of Protease-activated Receptors 2 and 4", The Journal of Biological Chemistry, vol. 279, No. 14, Apr. 2004, pp. 13532 to 13539. Cited in the ISR.
International Search Report of PCT/JP2005/023852, date of mailing Mar. 28, 2006.
Santagada, V. et al.: Minimal Strcuctural Requirements for Agonist Activity of PAR-2 Activating Peptides; Bioorg. Med. Chem. Lett. 12; pp. 21-24, 2002.
Nystedt, S. et al.; Molecular Cloning of a Potential Proteinase Activated Receptor; Proceeding of the National Academy of Sciences USA, 91: pp. 9208-9212, 1994.
Macfarlane, Scott R.. et al.; Proteinase-Activated Receptors; Pharmacological Reviews, 53; pp. 245-282, 2001.
Roy, Samir S.; Dual endothelium-dependent vascular activities of proteinase-activated receptor-2-activating peptides: evidence for receptor heterogeneity; Br J Pharmacol, 123; 1434-1440, 1998.
Kawabata, A. et al.; Increased vascular permeability by a specific agonist of protease-activated receptor-2 in rat hindpaw; Br J Pharmacol, 125; 419-422,1998.
Al-ani, B. et al.; Proteinase-Activated Receptor 2 ($PAR_2$): Development of a Ligand-Binding Assay Correlating with Activation of $PAR_2$ by $Par_1$- and $PAR_2$- Derived Peptide Ligands[1]; The Journal of Pharmacology and Experimental Therapeutics, vol. 290; pp. 753-760, 1999.
Hollenberg, Morley D. et. al.; Proteinase-Activated Receptor-2 in Rat Aorta: Structural Requirements for Agonist Activity of Receptor-Activating Peptides; Molecular Pharmacology, 49, 229-233, 1996.
Translation of International Preliminary Report on Patentability mailed Jul. 12, 2007 of International Application No. PCT/JP2005/023852.
European Search Report dated Jun. 17, 2009 issued in corresponding European Application No. 06730381.8.

(Continued)

*Primary Examiner* — Julie Ha
(74) *Attorney, Agent, or Firm* — Westerman, Hattori, Daniels & Adrian, LLP

(57) ABSTRACT

A compound, or a salt or solvate thereof having a structure of Ar—CO-$AA^1$-$AA^2$-$AA^3$-$AA^4$-NH—X—$NR^1R^2$ is disclosed. Ar represents an optionally substituted phenyl group or an aromatic heterocyclic group; $AA^1$ represents a hydrophobic amino acid; $AA^2$ represents an unsubstituted amino acid containing 2 or more carbon atoms; $AA^3$ represents an unsubstituted amino acid containing 2 or more carbon atoms; $AA^4$ represents a hydrophobic amino acid; X represents a divalent saturated aliphatic hydrocarbon group having 2-6 carbon atoms; and $R^1$ and $R^2$ represent a saturated or unsubstituted aliphatic hydrocarbon group having 1-8 carbon atoms, or alternatively $R^1$ and $R^2$ may form a ring together with an adjacent nitrogen atom. A pharmaceutical composition for prevention/treatment of diseases associated with PAR-2 is also disclosed. The pharmaceutical composition includes the above compound, a salt or a solvate thereof and a pharmaceutically acceptable carrier.

10 Claims, No Drawings

OTHER PUBLICATIONS

Hollenberg M. D. et al., "Proteinase-Activated Receptors: Structural Requirements for Activity, Receptor Cross-Reactivity, and Receptor Selectivity of Receptor-Activating Peptides", Canadian Journal of Physiology and Pharmacology, 1997, pp. 832-841, vol. 75, abstract only.

European Search Report dated Jul. 6, 2009 issued in corresponding European Application No. 5822433.8.

Hollenberg, M. D. et al., "Proteinase-Activated Receptors: Structural Requirements for Activity, Receptor Cross-Reactivity, and Receptor Selectivity of Receptor-Activating Peptides", Canadian Journal of Physiology and Pharmacology, Jul. 1997, pp. 832-841, vol. 75.

Lashuel, H. A. et al., "Protofilaments, Filaments, Ribbons, and Fibrils from Peptidomimetic Self-Assembly: Implication for Amyloid Fibril Formation and Materials Science", Journal of The American Chemical Society, May 19, 2000, pp. 5262-5277, vol. 122, American Chemical Society.

Toru Sugaya et al.(Toru Kanke) ; "Characterization of Potent Protease-Activated Receptor-2 (PAR-2) Activating Peptide, 2-furoyl-LIGRL-NH2" Nov. 2004, p. 116, Dai 12 Kai The Pharmaceutical Society of Japan Iyakuhin Kagakubukai Nenkai.

* cited by examiner

PAR-2 AGONIST

TECHNICAL FIELD

The present invention relates to a PAR-2 agonist and a pharmaceutical compound for prophylactic/therapeutic against PAR-2 associated diseases including the PAR-2 agonist as an active ingredient and in particular relates to PAR-2 agonist useful for prevention of development and progress, amelioration of clinical state, treatment or the like, and development of pharmaceutical agent for fever, dryness of eye, corneal epithelial detachment, keratitis, corneal ulceration, conjunctival inflammation, dysfunction of masticatory, dysphagia, taste disorder, mouth odor, mouth discomfort, mouth infection, mouth inflammation, cardiovascular functional disorder, acute respiratory distress syndrome, peptic ulcer such as gastric ulceration and duodenal ulcer, gastric inflammation, visceral pain, diarrhea, enteritis such as ulcerative colitis, kidney disorder such as nephritis, pancreatitis, ulcer tissue, bone resorption, dysmenorrhea, premature labor, nephrosis, or symptom of low blood pressure.

PAR (Protease-activated receptor)-2 is one of the protease-activated receptor (PAR) belonging to a G protein-coupled receptor family of 7-times transmembrane type cloned in 1994 by Nystedt et al. (Proc. Natl. Acad. Sci. USA, 91, 9208-9212 (1994)). PAR is a receptor family characterized by cleaving a specific site of amino-acid sequence in N terminal of the molecule with a serine protease such as thrombin or trypsin, and then binding a newly exposed cleavage N terminal fragment to a ligand binding site in the same molecule to activate. Up to date, four types of PAR-1, PAR-2, PAR-3 and PAR-4 were cloned, PAR-1, PAR-3, and PAR-4 are revealed their functions as receptors related to platelet agglutination with thrombin. Although a PAR-2 has many similarities with other PARs in terms of structure and activation mechanism, it is suggested to be functionally discrete to other PAR since the PAR-2 is not activated by thrombin, and is activated by trypsin and tryptase.

PAR-2 is known to be activated by a tissue factor/factor VIIa, factor Xa, acrosin (a type of sperm protease) and trypsin-like serine protease identified by a rat brain, further to trypsin and tryptase(Pharmacological Rev. 53, 245-282, (2001), Br. J. Pharmacol., 123, 1434-1440 (1998)) and it is reported that PAR-2 activation is useful for prevention and treatment for decrease in saliva secretion, decrease in lacrimal secretion and alimentary diseases (Japanese Patent Application Laid-open No. 2001-064203, Japanese Patent Application Laid-open No. 2001-181208, Japanese Patent Application Laid-open No. 2001-233790, U.S. Pat. No. 5,888,529, and U.S. Pat. No. 5,958,407).

It is significant to obtain a simpler structure compound considering usefulness in the development of pharmaceutical preparation, while in biochemical experiment, a peptide (Tethered receptor agonist peptide : TRAP) consisted of mainly 6 amino acid such as Ser-Leu-Ile-Gly-Lys-Val (SEQ ID NO. 1)-OH, Ser-Leu-Ile-Gly-Lys-Val (SEQ ID NO. 2)-NH$_2$, Ser-Leu-Ile-Gly-Arg-Leu (SEQ ID NO. 3)-OH, Ser-Leu-Ile-Gly-Arg-Leu (SEQ ID NO. 4)-NH$_2$ or the like having same sequence with PAR-2 ligand as PAR-2 activator is widely used. Heretofore N$^{60}$-benzoyl-Arg(NO$_2$)-Leu-NH$_2$ as a low molecular PAR-2 agonist is reported, PAR-2 activation of this compound is about one of hundred action strength of TRAP (Bioorg. Med. Chem. Lett. 2002, 12, 21-24). As PAR-2 activating agent, a compound that N-terminal amino acid of TRAP substituted to acyl group such as 2-furoyl (WO 03/104268), it is expected to obtain a compound having more simplified structure. As one of the methods for simplifying TRAP structure, a method for reducing number of amino acid is assumed. In WO 96/23225 [(U.S. Pat. Nos. 5,763,575, 5,874,400) COR Therapeutics Inc.], a peptide consisted of 5 to 7 amino acid as PAR-2 activating agent is claimed, in case of a peptide consisted of 5 amino acids (AA$^1$-AA$^2$-AA$^3$-AA$^4$-AA$^5$) each amino acid is defined as AA$^1$: small amino acid or threonine, AA$^2$ and AA$^3$: neutral/nonpolar/large/non-aromatic amino acid, AA$^4$: small amino acid, AA$^5$: basic amino acid. Although these conditions were set, it is general for PAR-2 activation potency to decreased extremely in case of reducing amino acid of peptide consisted of 6 amino acids simply (Pharmacol. Rev. 2001, 53, 245-282, J. Pharmacol. Exp. Ther. 1999, 290, 753-760, Mol. Pharmacol. 1996. 49, 229-233). However, it is hardly difficult for producing a peptide consisted of 6 amino acids industrially, and a development of agonist having same or more activation with shorter peptide has been expected.

DISCLOSURE OF INVENTION

Accordingly, the object of the present invention is to provide a PAR-2 agonist having PAR-2 activation potency same as TRAP or more improved potency, even in case of reducing amino acid of peptide consisted. That is, the object of the present invention is to provide a PAR-2 agonist useful for prevention of development and progress, amelioration of clinical state, treatment or the like, and development of pharmaceutical agent for fever, dryness of eye, corneal epithelial detachment, keratitis, corneal ulceration, conjunctival inflammation, dysfunction of masticatory, dysphagia, taste disorder, mouth odor, mouth discomfort, mouth infection, mouth inflammation, cardiovascular functional disorder, acute respiratory distress syndrome, peptic ulcer such as gastric ulceration and duodenal ulcer, gastric inflammation, visceral pain, diarrhea, enteritis such as ulcerative colitis, kidney disorder such as nephritis, pancreatitis, ulcer tissue, bone resorption, dysmenorrhea, premature labor, nephrosis, or symptom of low blood pressure.

In view of the circumstances described above, the present inventors made extensive study and as a result they found that a compound represented by the general formula (1) or a salt thereof or a solvate thereof have PAR-2 activation potency same as TRAP or more improved potency, and completed the present invention.

[General Formula 1]

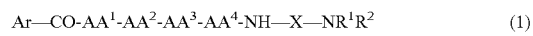

$$\text{Ar—CO-AA}^1\text{-AA}^2\text{-AA}^3\text{-AA}^4\text{-NH—X—NR}^1\text{R}^2 \qquad (1)$$

wherein Ar represents a phenyl group or an aromatic heterocyclic group optionally having substituent(s);

AA$^1$ represents a hydrophobic amino acid;

AA$^2$ represents an amino acid absent of substituent(s) comprising more than two carbon atoms;

AA$^3$ represents an amino acid absent of substituent(s) comprising more than two carbon atoms;

AA$^4$ represents a hydrophobic amino acid;

X represents C$_2$-C$_6$ bivalent saturated aliphatic hydrocarbon group;

Each of R$^1$ and R$^2$ are same or independently represents C$_1$-C$_8$ saturated or unsaturated aliphatic hydrocarbon group, or R$^1$ and R$^2$ optionally form a ring together with the nitrogen atom adjacent to them.

Accordingly, the present invention provides the compound represented by the above-mentioned general formula (1), a salt thereof or a solvate thereof.

The present invention also relates to a pharmaceutical composition for prophylaxis and therapy of the PAR-2 associated diseases, which consists of a compound represented by the general formula (1), a salt thereof or a solvate thereof and a pharmaceutically acceptable carrier.

Further, the present invention relates to a pharmaceutical composition for prophylaxis and therapy of no less than one disease selected from fever, dryness of eye, corneal epithelial detachment, keratitis, corneal ulceration, conjunctival inflammation, dysfunction of masticatory, dysphagia, taste disorder, mouth odor, mouth discomfort, mouth infection, mouth inflammation, cardiovascular functional disorder, acute respiratory distress syndrome, peptic ulcer such as gastric ulceration and duodenal ulcer, gastric inflammation, visceral pain, diarrhea, enteritis such as ulcerative colitis, kidney disorder such as nephritis, pancreatitis, ulcer tissue, bone resorption, dysmenorrhea, premature labor, nephrosis, or symptom of low blood pressure, which consists of a compound represented by the general formula (1), a salt thereof or a solvate thereof and a pharmaceutically acceptable carrier.

Further, the present invention relates to a prophylactic/therapeutic method for PAR-2 associated diseases, which includes administering an effective amount of the compound (1) of the present invention, a salt thereof or a solvate thereof to patients having or likely to have the PAR-2 associated diseases.

Further, the present invention relates to a prophylactic/therapeutic method which includes administering an effective amount of the compound (1) of the present invention, a salt thereof or a solvate thereof to patients having or likely to have no less than one disease selected from fever, dryness of eye, corneal epithelial detachment, keratitis, corneal ulceration, conjunctival inflammation, dysfunction of masticatory, dysphagia, taste disorder, mouth odor, mouth discomfort, mouth infection, mouth inflammation, cardiovascular functional disorder, acute respiratory distress syndrome, peptic ulcer such as gastric ulceration and duodenal ulcer, gastric inflammation, visceral pain, diarrhea, enteritis such as ulcerative colitis, kidney disorder such as nephritis, pancreatitis, ulcer tissue, bone resorption, dysmenorrhea, premature labor, nephrosis, or symptom of low blood pressure.

Further, the present invention relates to a use of the compound (1) of the present invention, a salt thereof or a solvate thereof in producing a pharmaceutical composition for prophylaxis and therapy of the PAR-2 associated diseases.

Further, the present invention relates to the use of the compound (1) of the present invention, a salt thereof or a solvate thereof in producing a pharmaceutical composition for prophylaxis and therapy of no less than one disease selected from fever, dryness of eye, corneal epithelial detachment, keratitis, corneal ulceration, conjunctival inflammation, dysfunction of masticatory, dysphagia, taste disorder, mouth odor, mouth discomfort, mouth infection, mouth inflammation, cardiovascular functional disorder, acute respiratory distress syndrome, peptic ulcer such as gastric ulceration and duodenal ulcer, gastric inflammation, visceral pain, diarrhea, enteritis such as ulcerative colitis, kidney disorder such as nephritis, pancreatitis, ulcer tissue, bone resorption, dysmenorrhea, premature labor, nephrosis, or symptom of low blood pressure.

According to the present invention, a PAR-2 agonist which can be an effective prophylactic/therapeutic agent against various PAR-2 associated diseases can be provided. Consequently, the present invention relates to a use of the compound represented by the present invention compound (1), a salt thereof or a solvate thereof as PAR-2 agonist.

Further, the present invention relates to a use of the compound represented by the present invention compound (1), a salt thereof or a solvate thereof as an active ingredient of pharmaceutical composition for prophylaxis and therapy of no less than one disease selected from fever, dryness of eye, corneal epithelial detachment, keratitis, corneal ulceration, conjunctival inflammation, dysfunction of masticatory, dysphagia, taste disorder, mouth odor, mouth discomfort, mouth infection, mouth inflammation, cardiovascular functional disorder, acute respiratory distress syndrome, peptic ulcer such as gastric ulceration and duodenal ulcer, gastric inflammation, visceral pain, diarrhea, enteritis such as ulcerative colitis, kidney disorder such as nephritis, pancreatitis, ulcer tissue, bone resorption, dysmenorrhea, premature labor, nephrosis, or symptom of low blood pressure.

BEST MODE FOR CARRYING OUT THE INVENTION

Ar in the general formula (1) represents a phenyl group or an aromatic heterocyclic group optionally having substituent(s), preferably an aromatic heterocyclic group optionally having substituent(s). The aromatic heterocyclic group of the present invention is a monocyclic, a polycyclic or a condensed ring system group comprising 5 to 7 membered aromatic heterocyclic ring wherein at least one ring having one, or two or more hetero atom(s) selected from nitrogen, oxygen or sulfur. Preferable aromatic heterocyclic group is for example, a furyl group, a pyridyl group, a benzofuryl group, an isoxazoryl group, or an imidazolyl group.

The phenyl group and aromatic heterocyclic group as mentioned above may be unsubstituted, or optionally with substituent (s), the substituent (s) are $C_1$-$C_8$ straight-chain or branched alkyl group, preferably $C_1$-$C_6$, more preferably $C_1$-$C_3$, such as a methyl group, an ethyl group or a n-propyl group; an alkoxy group consisted of $C_1$-$C_8$ straight-chain or branched alkyl group, preferably $C_1$-$C_6$, more preferably $C_1$-$C_3$, such as a methoxy group or an ethoxy group; a halogen atom such as a bromine atom and a chlorine atom. Preferable substituted aromatic heterocyclic group is for example such as a bromofuryl group or a dimethylfuryl group.

The hydrophobic amino acids or the amino acid absent of substituent(s) comprising more than two carbon atoms of the present invention can be α-amino acid linked amino group to a position of carboxyl group, and is not limited to natural amino acid or not. For an amino acid having optical activity, it can be D-isomer, L-isomer or racemate, preferably L-amino acid.

The amino acid of $AA^1$ is a hydrophobic amino acid, substituted to a position of α-amino acid by $C_2$-$C_{20}$ straight-chain or branched, or cyclic saturated or unsaturated hydrocarbon group, preferably $C_2$-$C_{10}$, more preferably $C_3$-$C_{10}$.

The hydrocarbon group as mentioned above is for example $C_2$-$C_8$ straight-chain or branched alkyl group, preferably $C_2$-$C_6$, more preferably $C_3$-$C_6$, such as isopropyl group, 2-methylpropyl group and 1-methyl-propyl group;

$C_5$-$C_{20}$ saturated cycloaliphatic hydrocarbon group, preferably $C_5$-$C_{10}$, more preferably $C_6$-$C_{10}$ such as cyclohexylmethyl group and cyclohexylethyl group;

$C_7$-$C_{20}$ aromatic alphatic group (aralkyl group), preferably $C_7$-$C_{12}$, more preferably $C_7$-$C_{10}$, such as benzyl group and the like.

Examples of preferable $AA^1$ amino acid are β-cyclohexylalanine, phenylalanine, isoleucine, luecine, valine, more preferable $AA^1$ amino acid is β-cyclohexylalanine or phenylalanine.

$AA^2$ amino acid represents an amino acid absent of substituent(s) having more than two carbon atoms, preferably an amino acid absent of substituent (s) comprising more than one carbon atom. Examples of preferable $AA^2$ amino acid are glycine and glycine derivatives such as halogenated glycines, like glycine, α-fluoroglycine, α,α-difluoroglycine, more preferable $AA^2$ amino acid is glycine.

$AA^3$ amino acid represents an amino acid absent of substituent(s) having more than two carbon atoms, preferably an amino acid absent of substituent (s) comprising more than one carbon atom. Examples of preferable AA³ amino acid are glycine and glycine derivatives such as halogenated glycines, like glycine, α-fluoroglycine, α,α-difluoroglycine, more preferable AA² amino acid is glycine.

The amino acid of AA⁴ is a hydrophobic amino acid, substituted to α position of α-amino acid by $C_2$-$C_{20}$ straight-chain or branched, or cyclic saturated or unsaturated hydrocarbon group, preferably $C_2$-$C_{10}$, more preferably $C_3$-$C_{10}$.

The hydrocarbon group as mentioned above is for example, $C_2$-$C_8$ straight-chain or branched alkyl group, preferably $C_2$-$C_6$, more preferably $C_3$-$C_6$, such as isopropyl group, 2-methylpropyl group, and 1-methyl-propyl group;

$C_5$-$C_{20}$ saturated aliphatic-cycloaliphatic hydrocarbon group, such as cyclohexylmethyl group and cyclohexylethyl group, preferably $C_5$-$C_{10}$, more preferably $C_6$-$C_{10}$; or $C_7$-$C_{20}$ aromatic alphatic group (aralkyl group), preferably $C_7$-$C_{12}$, more preferably $C_7$-$C_{10}$, such as benzyl group and the like.

Examples of more preferable AA⁴ amino acid are β-cyclohexylalanine, phenylalanine, isoleucine, luecine, valine, more preferable, β-cyclohexylalanine, or phenylalanine.

Accordingly, AA¹ and AA⁴ amino acid in the general formula (1) are the same or independently a hydrophobic amino acid, preferably the same or independently β-cyclohexylalanine, phenylalanine, isoleucine, luecine, valine and the like. Further, AA² and AA³ amino acid in the general formula (1) are the same or independently an amino acid absent of substituent (s) having more than two carbon atoms, preferably the same or independently an amino acid absent of substituent(s) having more than one carbon atom such as glycine, α-fluoroglycine, α,α-difluoroglycine.

X in the general formula (1) is $C_2$-$C_6$ straight-chain or branched bivalent saturated aliphatic hydrocarbon group, preferably $C_2$-$C_4$, more preferably $C_2$-$C_3$, and preferably a straight-chain group represented by the following formula

—(CH$_2$)$_n$—

(wherein n represents number 2 to 6)

The bivalent saturated aliphatic hydrocarbon group is for example, ethylene group, propylene group, butylene group, 1-methylethylene group, 2-methylethylene group and the like. Preferable bivalent saturated aliphatic hydrocarbon group is ethylene group represented by the following formula

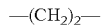
—(CH$_2$)$_2$—

R¹ and R² represented by the general formula (1) are the same or independently $C_1$-$C_8$ saturated or unsaturated aliphatic hydrocarbon group, preferably $C_1$-$C_6$, more preferably $C_1$-$C_3$, or a group optionally forms a ring together with the nitrogen atom adjacent to them. An aliphatic saturated hydrocarbon group is $C_1$-$C_8$ straight-chain or branched alkyl group, for example, methyl group, ethyl group, n-propyl group and the like, preferably $C_1$-$C_6$, more preferably $C_1$-$C_3$. Further, an unsaturated aliphatic hydrocarbon group is $C_2$-$C_8$ straight-chain or branched alkenyl group or alkynyl group, preferably $C_2$-$C_6$, more preferably $C_2$-$C_3$.

Wherein R¹ and R² form a ring together with the nitrogen atom adjacent to them, R¹ and R² form a 5 to 8 membered saturated or unsaturated alicyclic group having a carbon atom(s). These rings can be monocyclic, polycyclic or condensed, preferably monocyclic.

Preferable examples of —NR¹R² group represented by the general formula (1) are such as dimethylamino group, diethylamino group, di-n-propylamino group, diisopropylamino group, ethylmethylamino group, N-methyl-N-n-propylamino group, N-methyl-N-isopropylamino group, N-ethyl-N-n-isopropylamino group, N-ethyl-N-isopropylamino group, N-n-propyl-N-isopropylamino group, 1-pyrrolidinyl group, 1-piperidinyl group, more preferable example is 1-piperidinyl group.

The salt of the compound represented by the general formula (1) is not particularly limited insofar as it is a pharmaceutically acceptable salt, and preferably an acid addition salt, for example, mineral acid addition salt such as hydrochloride, hydrobromide, hydroiodide, sulfate and phosphate, and organic acid addition salt such as benzoate, methanesulfonate, ethanesulfonate, benzenesulfonate, p-toluenesulfonate, oxalate, maleate, fumarate, tartrate, citrate and acetate.

Further, when the compound represented by the general formula (1) is solvate forms such as hydrate, the compound also comprises the solvate. Further, when the compound represented by the general formula (1) has one or more than one asymmetric carbon atom(s), the present invention also comprises any configurational isomer(s).

The PAR-2 activation of peptide derivatives represented by the general formula (1) can be tested by known various methods. For example, PAR-2 activation of peptide derivates can be tested by the methods namely, "Hollenberg method" (Hollenberg, M. D., et al., Can. J. Physiol. Pharmacol., 75, 832-841 (1997)), "Kawabata et al. method" (Kawabata, A., et al., J. Pharmacol. Exp. Ther., 288, 358-370 (1999)), "Howthorne et al. method" (Howthorne et al., A High-Throughput Microtiter Plate-Based Calcium Assay for the Study of Protease-Activated Receptor 2 Activation, Analytical Biochemistry 290, 378-379 (2001)), and the like. The present inventors tested PAR-2 activation potency by the modified "Hawthorne et al. method". More specifically the method is to assay intracellular calcium dynamic expressing human PAR-2 inherently. In this assay, under probenecid inhibiting anion-exchange transporter the inventors measured intracellular calcium dynamic mediated PAR-2 agonist(concentration variation) by a multiple-well plate reader wherein introducing $Ca^{2+}$ sensitive fluorescent dye and stimulating this cell by PAR-2 agonist.

This method is explained below in more detail.

"HCT-15" which is a human colorectal adenocarcinoma cell line and which exhibits PAR-2 inherently at high level, was put into a 96-well black-wall clear-bottom plate and introduced $Ca^{2+}$ sensitive fluorescent dye (Calcium Assay Reagent, Molecular Devices), and cultured for 1 hour at 37° C. in a medium (RPMI) having 2.5 mM probenecid in a subconfluent cell without serum. Thereafter, the cells were stimulated with various concentration test compounds and measured at an excitation wavelength of 485 nm and at a measurement wavelength of 525 nm (cut-off 515 nm) with a fluorometer scanning a multiple well (Flex Station, Molecular Devices). As a comparative compound, SLIGKV-OH which is a known PAR-2 activated peptide was used. The results are shown in FIG. 1.

[FIG. 1]

| Compound (Example No.) | MW (Calculated value) | Agonist activity (EC50, μM) |
|---|---|---|
| Comparison compound (SLIGKV-OH) | — | 15.6 ± 0.9 |
| Example 1 | 642.83 | 16.5 ± 3.4 |
| Example 2 | 636.78 | 2.9 ± 0.6 |
| Example 3 | 721.73 | 0.7 ± 0.2 |

-continued

[FIG. 1]

| Compound (Example No.) | MW (Calculated value) | Agonist activity (EC50, μM) |
|---|---|---|
| Example 4 | 653.86 | 1.6 ± 0.1 |
| Example 5 | 692.89 | 0.8 ± 0.2 |
| Example 6 | 643.82 | 6.6 ± 3.1 |
| Example 7 | 653.86 | 7.6 ± 2.6 |
| Example 8 | 670.88 | 16.5 ± 2.1 |
| Example 9 | 642.83 | 14.9 ± 1.3 |

As a result, despite compounds of example 1, example 8 and example 9 extremely decreased number of amino acid(s), exhibited agonist activation almost same as the comparative peptide. Further, compounds of example 2 to example 7 exhibited stronger agonist activation than the comparative peptide.

A compound represented by the general formula (1) can be synthesized by forming five amide-linkages present in the molecule by amidations of an appropriate carboxylic acid and an appropriate amine in arbitrary order. After the production of the peptide portion by a conventional synthetic method for peptides, the amide-linkages can be introduced on the N-terminal and the C-terminal. However, in a preferable production process, for example, the dipeptide H-AA$^2$-AA$^3$-OH is synthesized initially, AA$^1$ is connected with this to form the peptide H-AA$^1$-AA$^2$-AA$^3$-OH, any protection is introduced if necessary, followed by acylation of the amimo group on the N-terminal to form N-acylated peptide represented by the general formula (2),

Ar—CO-AA$^1$-AA$^2$-AA$^3$-OH   (2)

(Wherein Ar, AA$^1$, AA$^2$ and AA$^3$ represent as mentioned above) and the product is reacted with the amino acid derivative represented by the general formula (3)

H-AA$^4$-NH—X—NR$^1$R$^2$   (3)

to produce the target compound represented by the general formula (1).

The amino acid derivative represented by the general formula (3) can be produced preferably by reacting the amino acid AA$^4$, amino group of which is protected, and the amine NH$_2$—X—NR$^1$—R$^2$.

As an N-acylation reaction and an amidation reaction, various amidation methods used for conventional peptide synthesis are applicable. Various methods such as solid-phase methods and solution-phase methods can be also used.

As for the amidation method of the present invention, arbitrary methods such as activted ester method and anhydride method for peptide synthesis can be applied, preferable amidation method is such as a method using a condensation reagent and a method using a reactive derivatve of the compound having a carboxyl group. The condensation reagent in the amidation are for example, 1,3-dicyclohexylcarbodiimide, 1-cyclohexyl-3-morpholinoethylcarbodiimide, 1-(3-diaminopropyl)-3-ethylcarbodiimide, 1,1'-carbonyldiimidazole, diethylphosphorocyanidate, diphenylphosphoryl azide, bis(2-oxo-3-oxazolydinyl)phosphonic chloride, 2-chloro-1-methylpyridinium iodine and the like. Further, the reactive derivatives of the compound having a carboxyl group are for example, an acyl halide such as acid chloride, acid azide, symmetric anhydride, or mixed anhydride formed with, for example, pivalic acid, an activated ester such as p-nitrophenyl ester and the like. If necessary, an appropriate base or appropriate solvent can be used when these reactions are carried out. The bases are an organic bases such as pyridine, triethylamine, and N,N-diisopropylethylamine, or an inorganic base such as sodium carbonate, and sodium hydrogencarbonate. The solvent is such as N,N-dimethylformamide, tetrahydrofuran, 1,4-dioxane, acetonitrile, methylene chloride, and 1,2-dichroloethane. Further, when a condensation reagent such as 1,3-dicyclohexylcarbodiimide is used it is effective to add an appropriate activating agent such as 1-hydroxybenzotriazole and N-hydroxysuccinimide for accelerating the reaction and inhibiting racemization. Further, to simplify an isolation operation of the synthesized peptide various reagents listed here can be modified for a solid-phase by binding on a resin such as polystyrene.

Further, in the process of synthesizing the compound represented by the general formula (1), if necessary, to inhibit unfavourable side reactions, functional groups present in starting materials and intermediates that should not engage with the expected reaction, can be protected and deprotected. As these protection and deprotection methods, a method used for conventional peptide synthesis is applicable. For instance, the protected carboxyl group is such as methyl ester, ethyl ester, t-butyl ester, and benzyl ester; and the protected amino group is such as methyl carbamate, allyl carbamate, t-butyl carbamate, benzyl carbamate, 9-fluorenylmethyl carbamate, p-methoxybenzyl carbamate, a formamide, acetamide, 3-nitro-2-pyridinesulfenamide, phthalimide. According to each properties, these protecting groups can be removed by acid treatment, base treatment, reduction, hydrolysis and the like. The acid in these methods is hydrogen chloride, hydrogen fluoride, methanesulfonic acid, trifluoromethanesulfonic acid, trifluoroacetic acid, trimethylsilyl bromide, trimethylsilyl trifluoromethanesulfonate, tetrafuloroboric acid, boron tribromide and the like; and the base is piperidine, pyrrolidine, triethylamine, N,N-diisopropylethylamine and the like. Further, in reductive condition, sodium/liquid ammonia, palladium catalyst/hydrogen, palladium catalyst/formic acid and the like are used; and in hydrolysis condition, lithium hydroxide, sodium hydroxide and the like are used.

The compound relating to the present invention obtained by the above method, if necessary, can be purified by the usual method, for example gel chromatography, partition chromatography, ion-exchange chromatography, affinity chromatography, countercurrent chromatography, high-performance liquid chromatography with various absorbents, or recrystallization and the like. Further, if necessary, the compound can be changed to the above-mentioned expected salt and solvate in the usual manner. The more specific examples of the method producing the compound represented by the general formula (1) are described in more detail by reference to the Examples.

The pharmaceutical composition of the present invention contains the compound represented by the general formula (1), a salt thereof and a solvate thereof as the active ingredient, and the administration form is not particularly limited and can be suitably selected depending the therapeutic purpose, and the pharmaceutical composition can be for example an oral agent, an injection, a suppository, an ointment, an inhalant, eye drops, nasal drops, and an adhesive preparation, and the composition suitable for these administration forms can be produced by incorporating a pharmaceutically acceptable carrier into the active ingredient according to a preparation method known to those skilled in the art.

When an oral solid preparation is produced, tablets, coated tablets, granules, powder, capsules or the like can be produced in a usual manner after an excipient, if necessary a binder, a disintegrating agent, a lubricant, a coloring agent, a flavoring substance, a fragrant substance and the like are added to the compound represented by the general formula (1) of the present invention. Such additives may be those generally used in the art; for example, the excipient includes lactose, sucrose, sodium chloride, glucose, starch, calcium carbonate, kaolin, microcrystalline cellulose, silicic acid and the like, the binder includes water, ethanol, propanol, simple syrup, glucose solution, starch solution, gelatin solution, carboxymethyl cellulose, hydroxypropyl cellulose, hydroxypropyl starch, methyl cellulose, ethyl cellulose, shellac, calcium phosphate, polyvinylpyrrolidone and the like, the disintegrating agent includes dry starch, sodium alginate, powdered agar, sodium hydrogen carbonate, calcium carbonate, sodium lauryl sulfate, monoglyceride stearate, lactose and the like, the lubricant includes purified talc, stearate, borax, polyethylene glycol and the like, and the flavoring substance includes sucrose, wild orange peel, citric acid, tartaric acid and the like.

When an oral liquid preparation is prepared, an oral liquid for internal use, syrup, elixir and the like can be produced in a usual manner by adding a flavoring substance, a buffer agent, a stabilizer, a fragrant substance and the like to the compound represented by the general formula (1) of the present invention. In this case, the flavoring substance may be the one described above, and the buffer agent includes sodium citrate and the like, and the stabilizer includes tragacanth, gum arabic, gelatin and the like.

When the injection is prepared, subcutaneous, intramuscular and intravascular injections can be produced in a usual manner by adding a pH adjusting agent, a buffer agent, a stabilizer, a tonicity agent, a topical anesthetic agent or the like to the compound represented by the general formula (1) of the present invention. In this case, the pH adjusting agent and the buffer agent include sodium citrate, sodium acetate, sodium phosphate and the like. The stabilizer includes sodium pyrosulfite, EDTA, thioglycolic acid, thiolactic acid and the like. The topical anesthetic agent includes procaine hydrochloride, lidocaine hydrochloride and the like. The tonicity agent can be exemplified by sodium chloride, glucose and the like.

When a suppository is prepared, it can be produced in a usual manner after pharmaceutical carriers known in the art, such as polyethylene glycol, lanolin, cacao seed oil, fatty acid triglyceride and the like and if necessary a surfactant such as Tween (registered trademark), are added to the compound represented by the general formula (1) of the present invention.

When an ointment is prepared, it can be produced in a usual manner by blending and mixing the compound represented by the general formula (1) of the present invention if necessary with usually used additives such as a base, a stabilizer, a moistening agent and a preservative. The base includes liquid paraffin, white petrolatum, Sarashi beeswax, octyldodecyl alcohol, paraffin and the like. The preservative includes methyl p-hydroxybenzoate, ethyl p-hydroxybenzoate, propyl p-hydroxybenzoate, and the like.

In addition to those described above, the compound (1) of the present invention can be formed in a usual manner into an inhalant, eye drops and nasal drops.

The amount of the active ingredient in the pharmaceutical composition of the invention administered varies depending on such as the age, sex, weight and symptom of the patient, therapeutic effect, treatment time, administration form, and administration frequency, and usually the compound (I) of the present invention is administered to an adult orally or parenterally in the range of 0.001 to 1000 mg, preferably 0.01 mg to 500 mg, more preferably 0.1 mg to 100 mg all at once or in divided portions per day. However, the dose varies depending on various conditions, and thus a dose lower than the above dose may be sufficient in some cases or a dose higher than the above range may be necessary in other cases. For example, the injection can be produced by dissolving or suspending the compound represented by the general formula (1) of the present invention at a concentration of 0.1 μg/mL to 10 mg/mL in a nontoxic pharmaceutically acceptable carrier such as physiological saline or commercial distilled water for injection.

The injection thus obtained can be administered in a dose of 1 μg to 100 mg, preferably 50 μg to 50 mg, for each administration, per body kg once to several times per day to a patient in need of treatment. The administration form can be exemplified by medically suitable administration forms such as intravenous injection, subcutaneous injection, intradermal injection, intramuscular injection and intraperitoneal injection. The intravenous injection is preferable. The injection can also be prepared as a suspension or emulsion with a non-aqueous diluent (for example, propylene glycol, polyethylene glycol and vegetable oils such as olive oil and alcohols such as ethanol) depending on the case. Sterilization of such injections can be carried out by filter sterilization, that is, through a bacteria-retaining filter, or with a sterilizer or through γ-ray irradiation. The injection can be produced by a form for preparation just before use. That is, a germ-free solid composition is produced by lyophilization and can be dissolved in germ-free distilled water for injection or other solvent just before use.

The thus obtained compound represented by the general formula (1) of the present invention has PAR-2 agonist action as shown later in the Test Example, therefore can be used as PAR-2 agonist, and is thus useful for prevention of development and progress, amelioration of clinical state, treatment and the like for the PAR-2-associated diseases, for example, fever, dryness of eye, corneal epithelial detachment, keratitis, corneal ulceration, conjunctival inflammation, dysfunction of masticatory, dysphagia, taste disorder, mouth odor, mouth discomfort, mouth infection, mouth inflammation, cardiovascular functional disorder, acute respiratory distress syndrome, peptic ulcer such as gastric ulceration and duodenal ulcer, gastric inflammation, visceral pain, diarrhea, enteritis such as ulcerative colitis, kidney disorder such as nephritis, pancreatitis, ulcer tissue, bone resorption, dysmenorrhea, premature labor, nephrosis, or symptom of low blood pressure.

Further, the compound represented by the general formula (1) is useful for prevention of development and progress, amelioration of clinical state, treatment for fever (rheumatic fever and influenza and other viral infection-related fever), common cold, dysmenorrheal, menstrual cramp, Crohn's disease, emphysema, acute respiratory distress syndrome, transplant toxic potency, dyscrasia, tissue ulcer, peptic ulcer, gastritis, diverticulitis, recurrent gastrointestinal lesion, gastrointestinal bleeding, blood coagulation, anemia, gout, ankylosing spondylitis, restenosis, periodontal disease, skin fragility, osteoporosis, prosthesis implant loosening, aortic aneurysm (abdominal aortic aneurysm and cerebral aortic aneurysm), periarteritis nodosa, congestive heart failure, spasm, head injury, spinal cord injury, neurogenerative disease (acute neurogenerating disease and chronic neurogenerating disease), Huntington's disease, Parkinson's disease, migraine headache, depression, peripheral neuropathy, gingivitis, cerebral amyloid angiopathy, nootropic or recognition enhancement, amyotrophic lateral sclerosis, multiple sclerosis, corneal injury, yellow spot degeneration, tendinitis, myasthenia gravis, polymyositis, myositis, bursitis, burn, diabetes mellitus (types I and type II diabetes mellitus, diabetic retinopathy), tumor invasion, tumor growth, tumor metastasis, corneal scar, scleritis, immunodeficiency disorders (for example, human AIDS and feline AIDS), sepsis, preterm delivery, hypoprothrombinemia, hemophila, thyroiditis, sarcoidosis, Bechet's syndrome, anaphylaxis kidney disorders and the like.

Hereinafter, the present invention is described in more detail by reference to the Examples, but the technical scope of the present invention is not limited to the Examples.

REFERENCE EXAMPLE 1

Production of 2-furoyl-β-cyclohexyl-L-alanyl-glycyl-glycine

[Chemical formula 1]

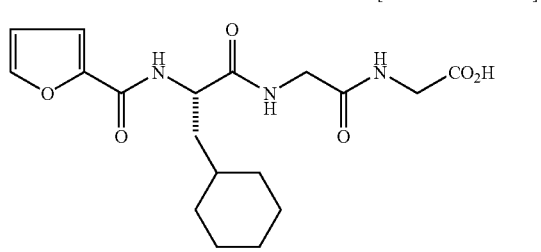

To a solution of 289.4 mg (1.47 mmol) of glycyl-glycine ethyl ester hydrochloride in anhydrous tetrahydrofuran (5 mL), 155.9 mg (1.54 mmol) of triethylamine, 451.5 mg (1.47 mmol) of N-t-butoxycarbonyl-β-cyclohexyl-L-alanine dihydrate, 205.3 mg (1.52 mmol) of 1-hydroxybenzotriazole hydrate, and 292.7 mg (1.53 mmol) of 1-[3-(dimethylaminomethyl)propyl]-3-ethylcarbodiimide hydrochloride were added sequentially with stirring under ice cooling. After the mixture was stirred for 1 hour, the reaction mixture was stirred at room temperature for 0.5 hour. The reaction mixture was concentrated under reduced pressure, chloroform (30 mL) was added to the residues, and the solution was washed sequentially with 0.5M hydrochloric acid (3×5 mL), water (3×5 mL) and 5% aqueous sodiumhydrogen carbonate solution (3×5 mL). The organic layer was dried over anhydrous sodium sulfate and concentrated under reduced pressure, whereby 570 mg of a crude product was obtained. The crude product was purified by column chromatography on alumina (alumina 2g, chloroform), to give 552.8 mg of N-t-butoxycarbonyl-β-cyclohexyl-L-alanyl-glycyl-glycine ethyl ester (yield 91%) as a colorless crystalline powder.

After 3.0 mL (12 mmol) of 4M hydrogenchloride/ethyl acetate solution was added to a solution of 506.2 mg (1.22 mmol) of N-t-butoxycarbonyl-β-cyclohexyl-L-alanyl-glycyl-glycine ethylester in ethyl acetate (1 mL) with stirring under ice cooling, the reaction mixture was stirred at room temperature for 4.5 hours. Diethyl ether (12 mL) was added to the mixture and the mixture was stirred under ice cooling. Then the precipitates were collected by filtration to obtain hygroscopic crude crystals. The crude crystals were suspended in diethyl ether (10 mL), and then collected by filtration, to give 370.3 mg of β-cyclohexyl-L-alanyl-glycyl-glycine ethyl ester hydrochloride (yield 86%) as a colorless crystalline power.

To a solution of 90.1 mg (0.258 mmol) of β-cyclohexyl-L-alanyl-glycyl-glycine ethyl ester hydrochloride in methylenechloride (1 mL), 100.0 mg (0.774 mmol) of N,N-diisopropylethylamine and 37.2 mg (0.285 mmol) of 2-furoyl chloride were added with stirring under ice cooling and the reaction mixture was stirred for 0.5 hour. Methanol (0.2 mL) was added and the reaction mixture was stirred at room temperature, and then concentrated under reduced pressure. Chloroform (25 mL) was added to the residue, and then the mixture was washed with 0.5M hydrochloric acid (3×5 mL) and 5% aqueous sodium hydrogencarbonate solution (3×5 mL). The organic layer was dried over anhydrous sodium sulfate and concentrated under reduced pressure, whereby 127 mg of the crude product was obtained. The crude product was purified by silica gel column chromatography [silica gel 7.5 g, chloroform, methanol-chloroform (1:100)], to give 103.2 mg of 2-furoyl-β-cyclohexyl-L-alanyl-glycyl-glycine ethyl ester as a colorless oil (yield 98%)

Water (0.1 mL) and 2.7 mg of lithium hydroxide hydrate (0.0643 mmol) were added to a solution of 22.5 mg of 2-furoyl-β-cyclohexyl-L-alanyl-glycyl-glycine ethyl ester (0.0552 mmol) in tetrahydrofuran (0.2 mL). After stirring for 1 hour at room temperature, water-ethanol (1:10, 0.5 mL) and 48.1 mg of IRC-50 (about 0.48 mg equivalent) were added and the mixture was stirred for 0.5 hour. IRC-50 (0.3 mg) was swelled in water-ethanol (1:10), and filled in a glass tube, and the mixture was placed on the column, and then the column was eluted by water-ethanol (1:10, 7.5 mL). The eluate was concentrated under reduced pressure, whereby 20.3 mg of the title compound was obtained as a colorless oil.

REFERENCE EXAMPLE 2

Production of β-cyclohexyl-L-alanine 2-(1-piperidinyl)ethyl amide

[Chemical formula 2]

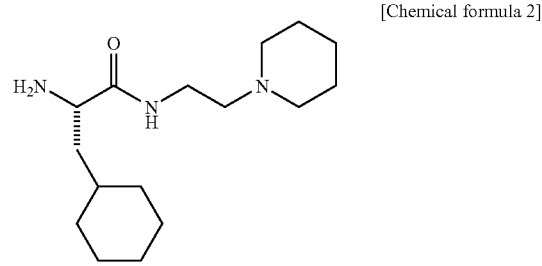

To a solution of 200.5 mg of N-t-butoxycarbonyl-β-cyclohexyl-L-alanine dihydrate (0.652 mmol) in tetrahydrofuran (1.5 mL), 101.7 mg of 1-(aminoethyl)piperidine (0.793 mmol), 89.7 mg of 1-hydroxybenzotriazole hydrate (0.664 mmol), and 146.1 mg of N,N'-dicyclohexylcarbodiimide (0.708 mmol) were added with stirring under ice cooling. The reaction mixture was stirred for 1 hour under ice cooling and for 1 hour at room temperature, and then concentrated under reduced pressure. Ethyl acetate (1 mL) was added to the residue. Insoluble materials were removed by filtration, and then the filtrate was concentrated under reduced pressure. The residue (438 mg) was purified by column chromatography on alumina (alumina 2 g, chloroform), whereby 267 mg of the crude product was obtained. The crude product was purified by silica gel column chromatography [silica gel 10 g, about 15% ammonia/methanol-chloroform (1:100)], whereby 240.0 mg of N-t-butoxycarbonyl-β-cyclohexyl-L-alanine 2-(1-piperidinyl)ethyl amide was obtained as a colorless oil (yield 96%)

To a solution (0.5 mL) of 233.3 mg of N-t-butoxycarbonyl-β-cyclohexyl-L-alanine 2-(1-piperidinyl)ethyl amide (0.611 mmol) in ethyl acetate, 1.5 mL of 4 M hydrogen chloride/ethyl acetate solution (6 mmol) was added and the reaction mixture was stirred for 4.5 hours at room temperature. The reaction mixture was concentrated under reduced pressure, and the residue was purified by column chromatography on alumina [alumina 2.5 g, methanol-chloroform (1:5)], whereby 167.7 mg of the title compound (97%) was obtained as a colorless oil (yield 97%).

EXAMPLE 1

Production of 2-furoyl-β-cyclohexyl-L-alanyl-glycyl-glycyl-β-cyclohexyl-L-alanyine 2-(1-piperidinyl) ethyl amide

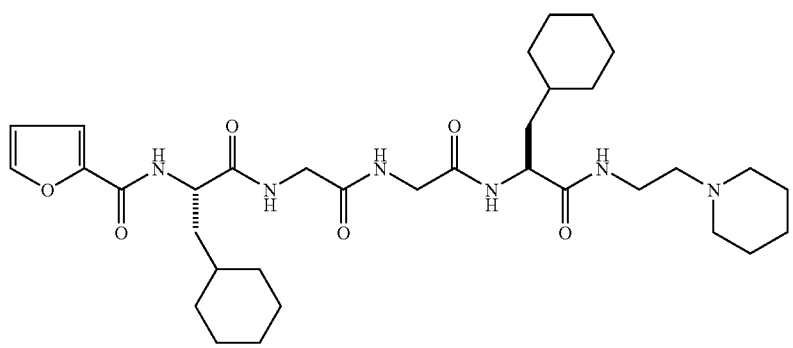

[Chemical formula 3]

Methylene chloride (0.5 mL) solution of 20.3 mg of 2-furoyl-β-cyclohexyl-L-alanyl-glycyl-glycine (0.055 mmol) produced in Reference Example 1 was stirred under ice cooling, and then N,N-dimethylformamide (0.5 mL) solution of 16.3 mg of β-cyclohexyl-L-alanine 2-(1-piperidinyl)ethyl amide (0.0579 mmol) produced in Reference Example 2, 8.1 mg of 1-hydroxybenzotriazole hydrate (0.060 mmol), and 11.6 mg of N,N'-dicyclohexylcarbodiimide (0.0562 mmol) were added. After stirring for 1 hour under ice cooling and for 12 hours at room temperature, chloroform (30 mL) was added and the reaction mixture was washed with aqueous saturated sodium hydrogencarbonate solution (3×5 mL). The organic layer was dried over anhydrous sodium sulfate and concentrated under reduced pressure, whereby 52.4 mg of crude oil was obtained. The crude oil was purified by silica gel thin-layer chromatography [about 15% ammonia/methanol-chloroform (1:10)] to give 30.5 mg of a colorless oil. The colorless oil was purified by column chromatography on alumina [alumina 0.2 g, methanol-chloroform (1:10)]) and recrystallized from hexane-ethyl acetate to give 24.3 mg of the title compound as a colorless crystalline powder (yield 75%)

Melting point: 192-194° C.

$^1$H-NMR (CDCl$_3$) δ: 7.48 (1 H, br.s), 7.15-7.32 (3 H, m), 7.14 (1 H, d, J=3.7 Hz), 6.96 (1 H, br. d, J=7.8 Hz), 6.70 (1 H, br. s), 6.51 (1 H, br. dd, J=2.0, 3.7 Hz), 4.60 (1 H, dt, J=8.6, 6.7 Hz), 4.45 (1 H, dt, J=6.3, 8.3 Hz), 4.06 (1 H, dd, J=6.0, 16.8 Hz), 3.97 (1 H, dd, J=6.0, 17.1 Hz), 3.89 (1 H, dd J=6.0, 17.1 Hz), 3.84 (1 H, dd, J=5.4, 16.8 Hz), 3.34 (1 H, dt, J=13.7, 5.9 Hz), 3.26 (1 H, dt, J=13.7, 5.6 Hz), 2.30-2.47 (6 H, m), 1.51-1.88 (18 H, m), 1.05-1.48 (9 H, m), 0.82-1.05 (5 H, m).

EXAMPLE 2

Production of 2-furoyl-L-phenylalanyl-glycyl-glycyl-β-cyclohexyl-L-alanine 2-(1-piperidinyl)ethyl amide

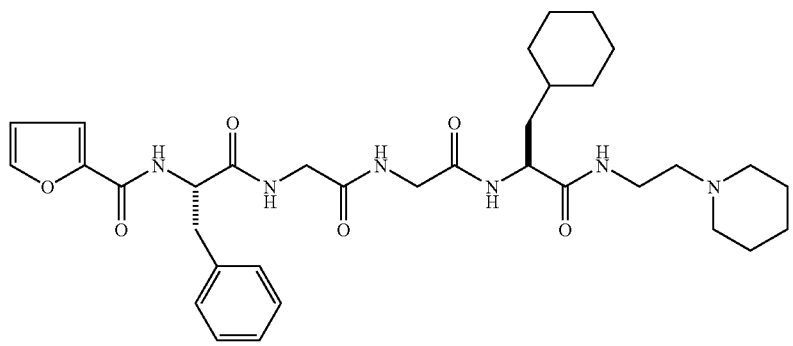

[Chemical formula 4]

2-Furoyl-L-phenylalanyl-glycyl-glycine was produced in the same manner as in Reference Example 1, by using L-phenylalanine in place of β-cyclohexyl-L-alanyl in Reference Example 1. In the same manner as Example 1, the title compound was obtained as a colorless crystalline powder from 2-furoyl-L-phenylalanyl-glycyl-glycine and β-cyclohexyl-L-alanine 2-(1-piperidinyl)ethyl amide produced in Reference Example 2.

Melting point: 183-187° C.

$^1$H-NMR [CD$_3$OD-CDCl$_3$ (1:10)] δ: 7.49 (1 H, br. s), 7.22-7.34 (5 H, m), 7.10 (1 H, br. d, J=3.5 Hz), 6.51 (1 H, dd, J=1.8, 3.5 Hz), 4.74 (1 H, br. t, J=7.3 Hz), 4.41 (1 H, br. dd, J=5.4, 9.5 Hz), 3.93 (1 H, br. d, J=16.8 Hz), 3.91 (1 H, br. d, J=16.8 Hz), 3.79 (1 H, br. d, J=16.8 Hz), 3.78 (1 H, br. d, J=16.8 Hz), 3.09-3.30 (4 H, m), 2.34-2.52 (6 H, m), 1.41-1.79 (13 H, m), 1.08-1.36 (4 H, m), 0.83-1.02 (2 H, m).

EXAMPLE 3

Production of 5-bromo-2-furoyl-β-cyclohexyl-L-alanyl-glycyl-glycyl-β-cyclohexyl-L-alanine 2-(1-piperidinyl)ethyl amide

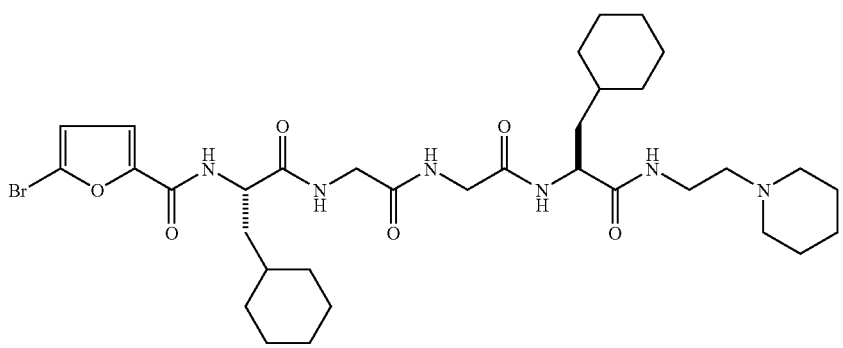

[Chemical formula 5]

In the same manner as Reference Example 1, 5-bromo-2-furoyl-β-cyclohexyl-L-alanyl-glycyl-glycine was produced by using 5-bromo-2-furoyl chloride in place of 2-furoyl chloride in Reference Example 1. In the same manner as Example 1, the tile compound was obtained as a colorless crystalline powder from 5-bromo-2-furoyl-β-cyclohexyl-L-alanyl-glycyl-glycine and β-cyclohexyl-L-alanine 2-(1-piperidinyl)ethyl amide produced in Reference Example 2.

Melting point: 107° C. (dec.)

$^1$H-NMR (CDCl$_3$) δ: 7.48 (1 H, br. s), 7.30 (1 H, br. s), 7.22 (1 H, br. d, J=7.5 Hz), 7.12 (1 H, br. d, J=8.5 Hz), 7.10 (1 H, d, J=3.4 Hz), 6.85H, br. s), 6.45 (1 H, d, J=3.4 Hz), 4.66 (1 H, dt, J=6.0, 8.7 Hz), 4.64 (1 H, dt, J=6.3, 8.2 Hz), 4.06 (1 H, dd, J=5.6, 16.8 Hz), 3.97 (2 H, dd, J=2.1, 5.6 Hz), 3.88 (1 H, dd, J=5.6, 16.8 Hz), 3.25-3.38 (2 H, m) 2.30-2.47 (6 H, m), 1.50-1.85 (18 H, m), 1.05-1.48 (9 H, m), 0.82-1.05 (5 H, m).

EXAMPLE 4

Production of nicotinoyl-β-cyclohexyl-L-alanyl-glycyl-glycyl-β-cyclohexyl-L-alanine 2-(1-piperidinyl)ethyl amide Nicotinoyl-β-cyclohexyl-L-alanyl-glycyl-glycine was produced in the same manner as Reference Example 1, by using nicotinoyl chloride in place of 2-furoyl chloride in Reference Example 1. The title compound was obtained as a colorless crystalline powder in the same manner as Example 1 from nicotinoyl-β-cyclohexyl-L-alanyl-glycyl-glycine and β-cyclohexyl-L-alanine 2-(1-piperidinyl)ethyl amide produced in Reference Example 2.

Melting powder: 122-126° C.

$^1$H-NMR (CDCl$_3$) δ: 9.12 (1 H, br. d, J=1.7 Hz), 8.69 (1 H, br. dd, J=1.7, 4.8 Hz), 8.22-8.30 (1 H, m), 8.20 (1 H, br. s), 8.18 (1 H, br. s), 7.84 (1 H, br. s), 7.52 (1 H, br. s), 7.43 (1 H, br. s), 7.35 (1 H, dd, J=4.8, 7.5 Hz), 4.91-5.01 (1 H, m), 4.59-4.60 (1 H, m), 4.09-4.13 (3 H, m), 3.98 (1 H, dd, J=4.8, 17.0 Hz), 3.33 (1 H, dt, J=13.4, 5.8 Hz), 3.16 (1 H, dt, J=13.4, 4.8 Hz), 2.27-2.44 (6 H, m) 1.49-1.72 (18 H, m), 1.04-1.32 (9 H, m), 0.78-1.04 (5 H, m).

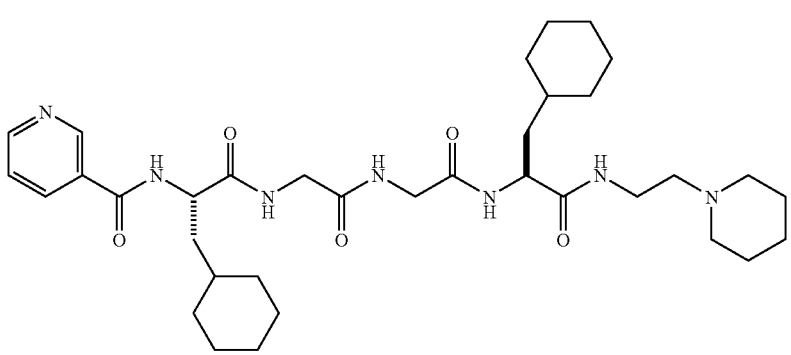

[Chemical formula 6]

EXAMPLE 5

Production of benzofuran-2-carbonyl-β-cyclohexyl-L-alanyl-glycyl-glycyl-β-cyclohexyl-L-alanine 2-(1-piperidinyl)ethyl amide

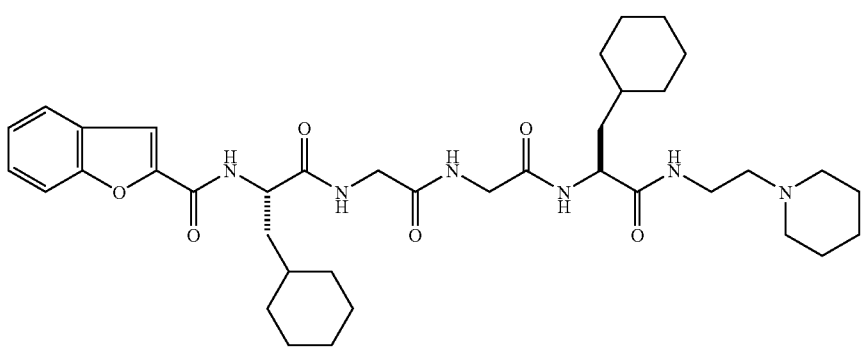

[Chemical formula 7]

Benzofuran-2-carbonyl-β-cyclohexyl-L-alanyl-glycyl-glycine was produced in the same manner as Reference Example 1, by using benzofuran-2-carbonyl chloride in place of 2-furoyl chloride in Reference Example 1. The title compound was obtained as a colorless crystalline powder in the same manner as Reference Example 1 from benzofuran-2-carbonyl-β-cyclohexyl-L-alanyl-glycyl-glycine and β-cyclohexyl-L-alanine 2-(1-piperidinyl)ethyl amide produced in Reference Example 2.

Melting point: 199° C. (dec)

$^1$H-NMR (CDCl$_3$) δ: 7.66 (1 H, br. d, J=7.3 Hz), 7.48-7.54 (2 H, m), 7.40-7.46 (3 H, m), 7.27-7.32 (2 H, m), 7.03 (1 H, br. d, J=8.2 Hz), 6.75 (1 H, br. s), 4.68 (1 H, dt, J=8.7, 6.8 Hz), 4.55 (1 H, dt, J=6.3, 8.5 Hz), 4.09 (1 H, dd, J=6.0, 16.8 Hz), 3.99 (1 H, dd, J=5.8, 17.0 Hz), 3.93 (1 H, dd, J=5.6, 17.0 Hz), 3.87 (1 H, dd, J=5.3, 16.8 Hz), 3.25 (1 H, dt, J=12.6, 6.3 Hz), 3.22 (1 H, dt, J=12.6, 6.0 Hz), 2.30-2.43 (6 H, m) 1.50-1.88 (18 H, m), 1.08-1.49 (9 H, m), 0.82-1.08 (5 H, m)

EXAMPLE 6

Production of isoxazole-3-carbonyl-β-cyclohexyl-L-alanyl-glycyl-glycyl-β-cyclohexyl-L-alanine 2-(1-piperidinyl)ethyl amide Isoxazole-3-carbonyl-β-cyclohexyl-L-alanyl-glycyl-glycine was produced in the same manner as Reference Example 1, by using isoxazole-3-carbonyl chloride in place of 2-furoyl chloride in Reference Example 1. The title compound was obtained as a colorless crystalline powder in the same manner as Example 1 from isoxazole-3-carbonyl-β-cyclohexyl-L-alanyl-glycyl-glycine and β-cyclohexyl-L-alanine 2-(1-piperidinyl)ethyl amide produced in Reference Example 2.

Melting point: 106° C. (dec)

$^1$H-NMR (CDCl$_3$) δ: 8.32 (1 H, d, J=1.7 Hz), 8.04 (1 H, br. s), 7.67 (1 H, br. s), 7.44 (1 H, br. s), 7.20 (1 H, br. d, J=7.0 Hz), 6.98 (1 H, br. s), 6.95 (1 H, d, J=1.7 Hz), 4.64-4.76 (1 H, m), 4.28-4.45 (1 H, 4.08 (1 H, br. dd, J=5.6, 16.3 Hz), 3.96-4.02 (1 H, m), 3.94 (1 H, br. dd, J=5.6, 19.5 Hz), 3.77-3.89 (1 H, m), 3.38-3.41 (1 H, m), 3.26-3.38 (1 H, m)), 3.26-3.38 (1 H, m), 2.37-2.65 (6 H, m) 1.52-1.95 (18 H, m), 1.05-1.52 (9 H, m), 0.80-1.05 (5 H, m).

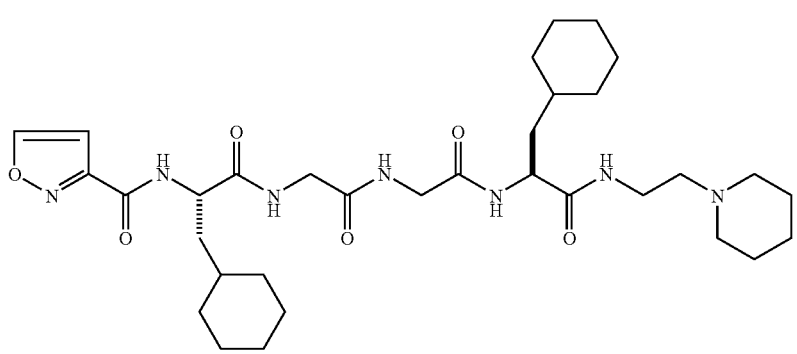

[Chemical formula 8]

EXAMPLE 7

Production of picolinoyl-β-cyclohexyl-L-alanyl-glycyl-glycyl-β-cyclohexyl-L-alanine 2-(1-piperidinyl)ethyl amide

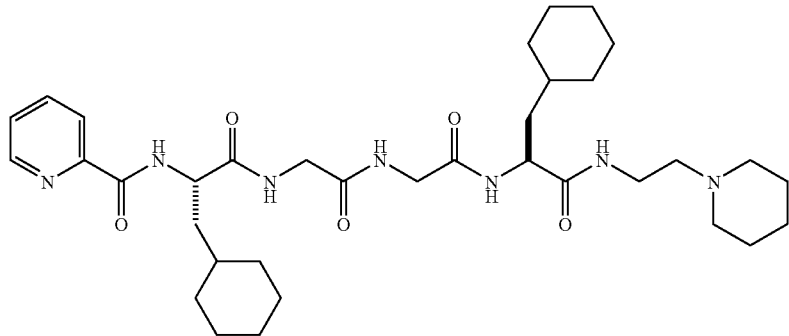

[Chemical formula 9]

Picolinoyl-β-cyclohexyl-L-alanyl-glycyl-glycine was produced in the same manner as Reference Example 1, by using picolinoyl chloride in place of 2-furoyl chloride in Reference Example 1. The title compound was obtained as a colorless crystalline powder in the same manner as Reference Example 1 from picolinoyl-β-cyclohexyl-L-alanyl-glycyl-glycine and β-cyclohexyl-L-alanine 2-(1-piperidinyl)ethyl amide produced in Reference Example 2.

Melting point: 158-162° C.

$^1$H-NMR (CDCl$_3$) δ: 8.59 (1 H, br. d, J=4.6 Hz), 8.44 (1 H, br. d, J=6.3 Hz), 8.12 (1 H, br. d, J=7.8 Hz), 7.87 (1 H, br. dd, J=1.4, 7.8 Hz), 7.54 (1 H, br. s), 7.47 (1 H, br. dd, J=4.6, 7.8 Hz), 6.98 (1 H, br. d, J=8.2 Hz), 6.77 (1 H, br. s), 4.52 (1 H, dt, J=9.2, 6.0 Hz), 4.46 (1 H, dt, J=5.6, 8.2 Hz), 3.97-4.09 (2 H, m), 3.86-3.96 (2 H, m), 3.29 (1 H, dt, J=5.8, 5.8 Hz), 3.28 (1 H, dt, J=5.8, 5.6 Hz), 2.32-2.50 (6 H, m) 1.50-1.95H, m), 1.10-1.50 (9 H, m), 0.85-1.10 (5 H, m).

EXAMPLE 8

Production of 4,5-dimethyl-2-furoyl-β-cyclohexyl-L-alanyl-glycyl-glycyl-β-cyclohexyl-L-alanine 2-(1-piperidinyl)ethyl amide 4,5-Dimethyl-2-furoyl-β-cyclohexyl-L-alanyl-glycyl-glycine was produced in the same manner as Reference Example 1, by using 4,5-dimethyl-2-furoyl chloride in place of 2-furoyl chloride in Reference Example 1. The title compound was obtained as a colorless amorphous powder in the same manner as Example 1 from 4,5-dimethyl-2-furoyl-β-cyclohexyl-L-alanyl-glycyl-glycine and β-cyclohexyl-L-alanine 2-(1-piperidinyl)ethyl amide produced in Reference Example 2.

$^1$H-NMR (CDCl$_3$) δ: 7.46 (1 H, br. s), 7.41 (1 H, br. s), 7.10 (1 H, br. d, J=8.0 Hz), 6.97 (1 H, br. d, J=7.0 Hz), 6.91 (1 H, s), 4.55 (1 H, dt, J=9.0, 6.3 Hz), 4.45 (1 H, dt, J=5.8, 8.5 Hz), 4.05 (1 H, dd, J=6.0, 16.8 Hz), 3.93 (2 H, br. dd, J=1.9, 5.8 Hz), 3.84 (1 H, dd, J=5.3, 16.8 Hz), 3.31 (1 H, dt, J=5.8, 5.8 Hz), 3.29 (1 H, dt, J=5.8, 5.6 Hz), 2.30-2.45 (6 H, m), 2.25 (3H, s), 1.95 (3 H, s), 1.50-1.85 (18 H, m), 1.05-1.50 (9 H, m), 0.80-1.05 (5 H, m).

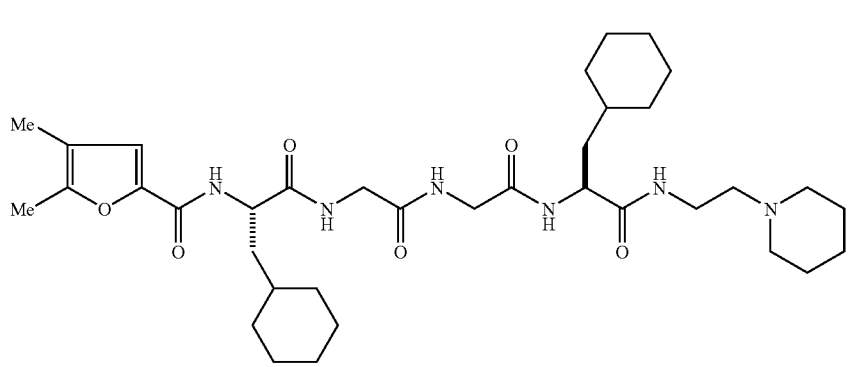

[Chemical formula 10]

EXAMPLE 9

Production of imidazole-4-carbonyl-β-cyclohexyl-L-alanyl-glycyl-glycyl-β-cyclohexyl-L-alanine 2-(1-piperidinyl)ethyl amide

[Chemical formula 11]

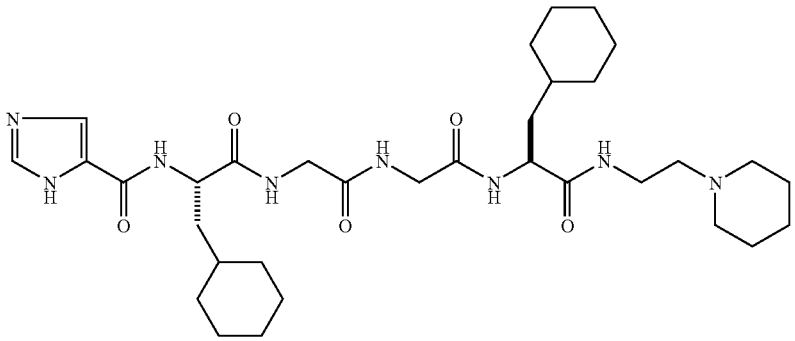

Imidazole-4-carbonyl-β-cyclohexyl-L-alanyl-glycyl-glycine was produced in the same manner as Reference Example 1, by using imidazole-2-carbonyl chloride in place of 2-furoyl chloride in Reference Example 1. The tile compound was obtained as a colorless crystalline powder in the same manner as Reference Example 1 from imidazole-4-carbonyl-β-cyclohexyl-L-alanyl-glycyl-glycine and β-cyclohexyl-L-alanine 2-(1-piperidinyl)ethyl amide produced in Reference Example 2.

Melting point: 129-138° C. (dec)

$^1$H-NMR [$CD_3OD$-$CD_3Cl$ (1:5)] δ: 7.61 (1 H, d, J=0.9 Hz), 7.58 (1 H, d, J=0.9 Hz), 4.38 (1 H, br. dd, J=5.6, 9.2 Hz), 4.37 (1 H, br. dd, J=5.1, 9.5 Hz), 3.97 (1 H, br. s), 3.93 (1 H, br. s), 3.87 (2 H, br. dd, J=4.6, 16.8 Hz), 3.30 (1 H, br. dt, J=13.6, 7.3 Hz), 3.28 (1 H, br. dt, J=13.6, 7.0 Hz), 2.38-2.58 (6 H, m), 1.50-1.85 (18 H, m), 1.05-1.50 (9 H, m), 0.80-1.05 (5 H, m).

INDUSTRIAL APPLICABILITY

According to the present invention, there can be provided PAR-2 agonist having PAR-2 activation potency same as TRAP or more improved potency, even in case of reducing amino acid of peptide consisted, and thus can be provided a useful compound having PAR-2 agonist action. Further, there can be also provided PAR-2 agonist useful for prevention of development and progress, amelioration of clinical state, treatment or the like, and PAR-2 agonist useful for pharmaceutical development, for the PAR-2 associated diseases, for example, fever, dryness of eye, corneal epithelial detachment, keratitis, corneal ulceration, conjunctival inflammation, dysfunction of masticatory, dysphagia, taste disorder, mouth odor, mouth discomfort, mouth infection, mouth inflammation, cardiovascular functional disorder, acute respiratory distress syndrome, peptic ulcer such as gastric ulceration and duodenal ulcer, gastric inflammation, visceral pain, diarrhea, enteritis such as ulcerative colitis, kidney disorder such as nephritis, pancreatitis, ulcer tissue, bone resorption, dysmenorrhea, premature labor, nephrosis, or symptom of low blood pressure. Thus, the compound and pharmaceutical composition of the present invention is industrially useful.

The invention claimed is:

1. A compound or a salt thereof, comprising:
a structure of general formula (1):

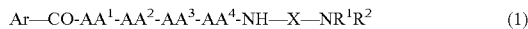

$Ar-CO-AA^1-AA^2-AA^3-AA^4-NH-X-NR^1R^2$    (1)

wherein Ar represents a phenyl group or an aromatic heterocyclic group, the phenyl group or an aromatic heterocyclic group optionally having substituent(s) selected from the group consisting of $C_1$-$C_8$ straight-chain or branched alkyl group, an alkoxy group consisting of $C_1$-$C_8$ straight-chain or branched alkyl group, and halogen atom(s);

wherein $AA^1$ represents a hydrophobic amino acid selected from the group consisting of β-cyclohexylalanine, phenylalanine, isoleucine, luecine, and valine;

wherein $AA^2$ represents an amino acid selected from the group consisting of glycine, α-fluoroglycine, and α,α-difluoroglycine;

wherein $AA^3$ represents an amino acid selected from the group consisting of glycine, α-fluoroglycine, and α,α-difluoroglycine;

wherein $AA^4$ represents a hydrophobic amino acid selected from the group consisting of β-cyclohexylalanine, phenylalanine, isoleucine, luecine, and valine;

wherein X represents a straight-chain group represented by the following formula:

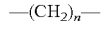

$-(CH_2)_n-$ wherein n represents integer number 2 to 6; and wherein $-NR^1R^2$ group is selected from the group consisting of a dimethylamino group, diethylamino group, di-n-propylamino group, diisopropylamino group, ethylmethylamino group, N-methyl-N-n-propylamino group, N-methyl-N-isopropylamino group, N-ethyl-N-n-isopropylamino group, N-ethyl-N-isopropylamino group, N-n-propyl-N-isopropylamino group, 1-pyroridinyl group, and 1-piperidinyl group.

2. The compound or a salt thereof according to claim 1, wherein Ar in the general formula (1) is a furyl group, pyridyl group, benzofuryl group, isoxazoryl group, imidazolyl group, buromofuryl group or dimethylfuryl group.

3. The compound or a salt thereof according to claim 1, wherein each of amino acids $AA^1$ and $AA^4$ in the general formula (1) is selected from the group consisting of β-cyclohexylalanine and phenylalanine.

4. The compound or a salt thereof according to claim 3, wherein amino acid $AA^4$ is β-cyclohexylalanine.

5. The compound or a salt thereof according to claim 4, wherein amino acids $AA^2$ and $AA^3$ in the general formula (1) are glycine.

6. The compound or a salt thereof according to claim 1 wherein X is an ethylene group.

7. The compound or a salt thereof according to claim 1 wherein $-NR^1R^2$ in the general formula (1) is the 1-piperidinyl group.

8. The compound or a salt thereof according to claim 1, wherein the compound is selected from the group consisting of 2-furoyl-β-cyclohexyl-L-alanyl-glycyl-glycyl-β-cyclohexyl-L-alanine 2-(1-piperidinyl)ethylamide, 2-furoyl-L-phenylalanyl-glycyl-glycyl-β-cyclohexyl-L-alanine 2-(1-piperidinyl)ethylamide, 5-bromo -2-furoyl-β-cyclohexyl-L-alanyl-glycyl-glycyl-β-cyclohexyl-L-alanine 2-(1-piperidinyl)ethylamide, nicotinoyl-β-cyclohexyl-L-alanyl-glycyl-glycyl-β-cyclohexyl-L-alanine 2-(1-piperidinyl)ethylamide, benzofuran-2-carbonyl-β-cyclohexyl-L-alanyl-glycyl-glycyl-β-cyclohexyl-L-alanine 2-(1-piperidinyl)ethylamide, isoxazole-3-carbonyl-β-cyclohexyl-L-alanyl-glycyl-glycyl-β-cyclohexyl-L-alanine 2-(1-piperidinyl)ethylamide, picorinoyl-β-cyclohexyl-L-alanyl-glycyl-glycyl-β-cyclohexyl-L-alanine 2-(1-piperidinyl)ethylamide, 4,5-dimethyl-2-furoyl-β-cyclohexyl-L-alanyl-glycyl-glycyl-β-cyclohexyl-L-alanine 2-(1-piperidinyl)ethylamide, and imidazole-2-carbonyl-β-cyclohexyl-L-alanyl-glycyl-glycyl-β-cyclohexyl-L-alanine 2-(1-piperidinyl)ethylamide.

9. A pharmaceutical composition comprising:
a compound or a salt thereof according to claim 1, and
a pharmaceutically acceptable carrier.

10. A method of treating a PAR-2 associated disease, comprising: administering an effective amount of the compound or a salt thereof according to claim 1, to patients having the PAR-2 associated disease, wherein the disease is selected from the group consisting of fever, dryness of eye, corneal epithelial detachment, keratitis, corneal ulceration, conjunctival inflammation, dysfunction of masticatory, dysphagia, taste disorder, mouth odor, mouth discomfort, mouth infection, mouth inflammation, cardiovascular functional disorder, acute respiratory distress syndrome, peptic ulcer, gastric ulceration, duodenal ulcer, gastric inflammation, visceral pain, diarrhea, enteritis, ulcerative colitis, kidney disorder, nephritis, pancreatitis, ulcer tissue, bone resorption, dysmenorrhea, premature labor, nephrosis, and symptom of low blood pressure.

* * * * *

```
                        SEQUENCE LISTING

<160> NUMBER OF SEQ ID NOS: 4

<210> SEQ ID NO 1
<211> LENGTH: 6
<212> TYPE: PRT
<213> ORGANISM: Artificial Sequence
<220> FEATURE:
<223> OTHER INFORMATION: Synthetic peptide

<400> SEQUENCE: 1

Ser Leu Ile Gly Lys Val
1               5

<210> SEQ ID NO 2
<211> LENGTH: 6
<212> TYPE: PRT
<213> ORGANISM: Artificial Sequence
<220> FEATURE:
<223> OTHER INFORMATION: Synthetic polypeptide
```

```
<400> SEQUENCE: 2

Ser Leu Ile Gly Lys Val
1               5

<210> SEQ ID NO 3
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 3

Ser Leu Ile Gly Arg Leu
1               5

<210> SEQ ID NO 4
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 4

Ser Leu Ile Gly Arg Leu
1               5
```